United States Patent
Zhukov et al.

(10) Patent No.: US 7,655,479 B2
(45) Date of Patent: Feb. 2, 2010

(54) LUMINESCENCE CHARACTERIZATION OF QUANTUM DOTS CONJUGATED WITH BIOMARKERS FOR EARLY CANCER DETECTION

(75) Inventors: Tatyana A. Zhukov, Lutz, FL (US); Sergei Ostapenko, Wesley Chapel, FL (US); Rebecca Sutphen, Tampa, FL (US); Johnathan Lancaster, Tampa, FL (US); Thomas A. Sellers, Tampa, FL (US); Jin Z. Zhang, Santa Cruz, CA (US)

(73) Assignees: University of South Florida, Tampa, FL (US); H. Lee Moffitt Cancer Center and Research Institute, Inc., Tampa, FL (US); The Regents of the University of California, Oakland, CA (US)

( * ) Notice: Subject to any disclaimer, the term of this patent is extended or adjusted under 35 U.S.C. 154(b) by 514 days.

(21) Appl. No.: 11/160,617

(22) Filed: Jun. 30, 2005

(65) Prior Publication Data

US 2006/0003465 A1    Jan. 5, 2006

Related U.S. Application Data

(60) Provisional application No. 60/584,021, filed on Jun. 30, 2004.

(51) Int. Cl.
G01N 33/551    (2006.01)
G01N 33/553    (2006.01)

(52) U.S. Cl. .................... 436/524; 436/512; 436/525; 436/64

(58) Field of Classification Search .............. None
See application file for complete search history.

(56) References Cited

U.S. PATENT DOCUMENTS

| 5,320,956 | A | 6/1994 | Willingham et al. |
| 6,306,610 | B1 * | 10/2001 | Bawendi et al. .......... 435/7.1 |
| 6,423,551 | B1 | 7/2002 | Weiss et al. |
| 2004/0023415 | A1 | 2/2004 | Sololov et al. |

OTHER PUBLICATIONS

Margaret A. Hines and Philippe Guyot-Sionnest, Synthesis and Characterization of Strongly Luminescing ZnS-Capped CdSe Nanocrystals, J. Phys, Chem. 1996, 100, p. 468-471.

Marcel Bruchez et al., Semiconductor Nanocrystals as Fluorescent Biological Labels, Science, vol. 281, 1998.

Ellen R. Goldman, Avidin: A Natural Bridge for Quantum Dot-Antibody Conjugates, J. Am. Chem. Soc., 2002, 124, p. 6378-6382.

B.O. Dabbousi et al., (CdSe) ZnS Core-Shell Quantum Dots: Synthesis and Characterization of a Size Series of Highly Luminescent Nanocrystallites, J. Phsy. Chem., 1997, 101, p. 9463-9475.

(Continued)

*Primary Examiner*—Christopher L Chin
(74) *Attorney, Agent, or Firm*—Robert Varkonyi; Smith & Hopen, P.A.

(57) ABSTRACT

Luminescent semiconductor quantum dots (QDs) conjugated with biomolecules to serve as sensitive probes for early detection of the cancer cells, specifically for ovarian cancer and lung cancer, which represents the most lethal malignancies. The luminescence characterization of the bin-conjugated QDs with cancer specific antigens using linkage molecules. Photo-enhancement is measured at various laser density power, temperatures and laser wavelengths.

10 Claims, 3 Drawing Sheets

OTHER PUBLICATIONS

J. Rodriguez-Viejo, Evidence of Photo-and Electrodarkening of (CdSe) ZnS Quantum Dot Composites, Journal of Applied Physcs, vol. 87, No. 12, 2000.

N.E. Korsunskaya et al., Photochemical Reactions at Low Temperatures in CdS Single Crystals, Phys. Stat. Sol., 13, p. 25-36, 1966.

Maria E. Akerman, Nanocrystal Targeting In Vivo, Proc. Nat'l Acad. Sci., vol. 99, No. 20, p. 12617-12621, 2002.

M.K. Sheinkman, The Recharge-Enhance Transformations of Donor-Acceptor Pairs and Clusters in CdS, J. Phys. Chem. Solids, vol. 43. No. 5, p. 475-479, 1982.

N.E. Korsunskaya et al., The Influence of Carrier Trapping on Defect Reaction Activation Energy in Semiconductors (Pesudo-Effect of Recombination Enhanced Diffusion), J. Phys. Chem. Solids, vol. 53, No. 3, p. 469-474, 1992.

C.A. Leatherdale, Photoconductivity in CdSe Quantum Dot Solids, The American Physical Society, vol. 62, No. 4, p. 26692680, 2000.

N.E. Korsunskaya et al., Photosensitivity Degradation Mechanism in CdS: Cu Single Crystals, Phys. Stat. Sol., vol. 60, p. 565-572, 1980.

Xingyong Wu et al., Immunofluorescent Labeling of Cancer Marker Her2 and Other Cellular Targets With Semiconductor Quantum Dots, Nature Biotechnology, vol. 21, p. 41-46, 2003.

Benoit Debertret, In Vivo Imaging of Quantum Dots Encapsulated in Phospholipid Micelles, Science, vol. 298, p. 1759-1762, 2002.

Juoti K. Jaiswal, Long-Term Multiple Color Imaging of Live Cells Using Quantum Dot Bioconjugates, Nature Biotechnology, vol. 21, p. 47-51, 2003.

A. Gartagdyev, Mechanism of Photostimulated Dissociation of Donor-Acceptor Pairs in CdS Crystals and in CdSxSe1-x Solid Soultion, American Institute of Physics, vol. 21, No. 3, p. 249-251, 1987.

D.I. Chepic, Auger Ionization of Semiconductor Quantum Drops in a Glass Matrix, Journal of Luminescence 47, p. 113-127, 1990.

Abbate I, et al. Tumor necrosis factor and soluble interleukin-2 receptor: Two immunological biomarkers in female neoplasm. Eur J Gynaecol Oncol 13(1 Suppl} p. 92-6, 1992.

Bergkessel M, Reese JC. An essential role for the *Saccharomyces cerevisiae* DEAD-box helicase DHH1 in G1/S DNA-damage checkpoint recovery. Genetics. May 2004;167(1}:21-33.

Berse B, Brown LF, Van De Water L, Dvorak HF, Senger DR Vascular permeability factor (vascular endothelial growth factor) gene is expressed differentially in normal tissues, macrophages, and tumors. Mol Biol Cell: 3(2) 211-20, 1992.

Campa MJ, et al. Protein expression profiling identifies macrophage migration inhibitory factor and cyclophilin a as potential molecular targets in non-small cell lung cancer. Cancer Res 63:1652-1656, 2003.

De Bruijn HW, Ten Hoor KA, Van Der Zee AG. Serum and cystic fluid levels of soluble iterleukin-2 receptor-alpha in patients with epithelial ovarian tumors are correlated. Tumour 1998, 19(3) p. 160-6.

Endoh H. Tomida S Yatahe Y. Konishi H, Osada H, Tajima K, Kuwano H, Takahashi T, Mitsudom! T, Prognostic model of pulmonary adenocarcinoma by expression profiling of eight genes as determined by quantitative real-time reverse transcriptase polymerase chain reaction J Clin Oncol. Mar. 1, 2004;22(5):811-9.

Gadducci A, et al. Elevated serum levels of neopterin and soluble interleukin-2 receptor in patients with ovarian cancer Gynecol Oncol, 52(3). p. 386-91 1994.

Gendler SJ, Spicer AP. Epithelial mucin genes Annu Rev Physiol 57: p. 607-34. 1995.

Geng Z. Zhang D, Liu Y. Expression of telomerase hTERT in human non-small cell lung cancer and its correlation with c-myc gene. Chinese Medical J. 116(10):1467-1470.2003.

Hara T. Ishida H. Raziuddin R, Dorkhom S, Kamijo K, Miki T., Mol Biol Cell Mar. 15, 2004(3}:1172-84. Epub Dec. 10, 2003.

Hsu CP, Miaw J, Hsia JY, Shai SE, Chen CY, Concordant expression of the telomerase-associated genes in non-small cell lung cancer. Europ J of Surgical Oncology, 29(7):594-599, 2003.

Hurteau JA, Simon UH, Kurman C, Rubin L, Mills, GB, Levels of soluble interleukin-2 receptor-alpha are elevated in serum and ascitic fluid from epithelial ovarian cancer patients, Am J Obstet Gynecol 170(3) p. 918-28., 1994.

Hurteau JA, Woolas RP, Jacobs IJ, Oram DC, Kurman CC, Rubin LA, Nelson DL, Berchuck A, Bast RC Jr, Mills GB. Soluble interleukin-2 receptor alpha is elevated in sera of patients with benign ovarian neoplasms and epithelial ovarian cancer. Cancer, 1995. 76(9) p. 1615-20.

Jang SJ, Soria JC, Wang L, et al. Activation of melanoma tumor antigens occurs early in lung carcinogenesis Cancer Res 61: 7959-7963, 2001.

Lagarde A, Forgach T, Nagy D, Nagy K, Vasas S, Janoki GA. Diagnostic sensitivity of three tumour markers in non-small cell lung cancer: a pilot study. Nucl Med Rev Cent East Eur:3(2): 139-42 2000.

Lantuejoul S, et al. Differential expression of telomerase reverse transcriptase (hTERT) in lung tumours Br J Cancer. Mar. 22,90(6)1222-9.2004.

Lendeckel U, Kohl J, Arndt M, Carl-McGrath S. Donat H, Rocken C. Increased expression of ADAM family members in human breast cancer and breast cancer cell lines. J Cancer Res Clin Oncol. 2005, 131(1):41-8.

Mecklenburg I, et al. Detection of melanoma antigen-A expression in sputum and bronchial lavage fluid of patients with lung cancer. Chest 125 S)164$-1 2004.

Mimnaugh EG, et al. Prevention of cisplatin-DNA adduct repair and potentiation of cisplatin-induced apoptosis in ovarian carcinoma cells by proteasome inhibitors Biochem Pharmacol. Nov. 1, 2000 ;60(9): 1343-54.

Neufeld G, Tessler S, Gitay-Goren H, Cohen T, Levi BZ, Vascular endothelial growth factor and its receptors. Prog Growth Factor Res 5(1): 89-97, 1994.

Payne M, Yang Z, Katz SJ, Warner JE, Weight CJ. Zhao Y, Pearson ED, Treft RL, Hillman T, Kennedy RJ, Meire FM. Zhang K. Am J Ophthalmol Nov. 2004;138(5) 749-55.

Powell BL, Toomes C, Scott S, Yeung A, Marchbank NJ, Spry PG, Lumb R, Inglehearn CF, Churchill AJ. Mol Vis Sep. 22, 2003:9:460-4.

Schmoll HJ, et al. European consensus on diagnosis and treatment of germ cell cancer a report of the European Germ Cell Cancer Consensus Group (EGCCCG) Ann Oncol Sep. 15, 2004:1377.99.

Sedlaczek P, et al. Comparative analysis of CA125, tissue polypeptide specific antigen, and soluble interleukin receptor alpha levels in sera, cyst, and ascitic fluids from patients with ovarian carcinoma. Cancer, 2002 95(9) p. 1886-93.

Senger DR, et al. The alpha(1)beta(1) and alpha(2)beta(1) integrins provide critical support for vascular endothelial growth factor signaling, endothelial cell and tumor angiogenesis. Am J Pathol, 2002. 160(1):195-204.

Song L, Turkson J, Karras JG, Jove R, Haura EB. Activation of Stat3 by receptor tyrosine kinases and cytokines regulates survival in human non-small cell carcinoma cells. Oncogene 22(27):4150-65, 2003.

Sozzi G, et al. Quantification of free circulating DNA as a diagnostic marker in lung cancer. J of Clin Oncol, 21 (21):3902-3908, 2003.

Sugita M, et al. Combined use of oligonucleotide and tissue microarrays identifies cancer/testis antigens as biomarkers in carcinoma. Cancer Res, 62 3971-3979, 2002.

Takahashi K, Takahashi F, Hirama M, Tanabe KK, Fukuchi Y. Restoration of CD44S in non-small cell lung cancer cells enhanced their susceptibility to the macrophage cytotoxicity. Lung Cancer 41 (2) 145-53, 2003.

Tamura M, et al. Plasma VEGF concentration can predict the tumor angiogenic capacity in non-small cell lung cancer. Oncol Rep. 8(5):1097-102, 2001.

Tamura M., et al. Chest CT and serum endothelial growth factor-C level to diagnose lymph node metastasis in patients with primary non-small cell lung cancer. Chest: 126(2):342-6, 2004.

Tockman MS. Survival and mortality from lung cancer in a screened population—the Johns Hopkins Study. Chest. 89:324S.325S, 1986.

Valle RC, Chavany C. Zhukov TA, Jendoubi M. New approaches for biomarker discovery in lung cancer. Expert Rev Mol Diagn, 355-67. 2003. Review.

Waldmann TA. The interleukin-2 receptor. J Biol Chem 266(5) p. 2681-4, 1991.

White ES, et al. Macrophage migration inhibitory factor and CXC chemokine expression in non-small cell lung cancer role in angiogenesis and prognosis. Clin Cancer Res, 9:853-860, 2003.

Yasumoto K., et al. Cancer-specific binding of a mouse MAb VS. *Candida krusei* cytochrome c: an antigen recognized by a cancer-associated human MAb HB4C5, Hum Antibodies Hybridomas Oct. 1993:4(4): 186.9.

Yeatman TJ, Chambers AF. Osteopontin and colon cancer progression. Clin Exp Metastasis, 2003, 20(1);85-90, Review.

Yoshimatsu T, Yoshino I, Ohgami A, et al. Expression of the melanoma antigen-encoding gene in human lung cancer. J Surg Oncol, 67: 126-129, 1998.

Zafarana G, et al. Coamplification of DAD-R, SOX5, and EKI1 in human testicular seminomas, with specific overexpression of DAD-R correlates with reduced levels of apoptosis and earlier clinical manifestation Cancer Res. Mar. 15, 2002:62(6) 1822-31.

Zhang J, Takahashi K, Takahashi F. Shimizu K. Ohshita, F, Kameda Y, Maeda K. Nishio K, Fukuchi Y. Differential osteopontin expression in lung cancer. Cancer Lett, 2001 , 171(2) 215-22.

Zhukov TA, Johanson RA, Cantor AB, Clark RA, Tockman MS. Discovery of distinct protein profiles specific for lung tumors and pre-malignant lung lesions by SELDI mass spectrometry. Lung Cancer, 40:267-279, 2003.

* cited by examiner

LUMINESCENCE CHARACTERIZATION OF QUANTUM DOTS CONJUGATED WITH BIOMARKERS FOR EARLY CANCER DETECTION

CROSS REFERENCE TO RELATED APPLICATIONS

This application claims priority to U.S. Provisional Patent Application No. 60/584,021, entitled, "Luminescence Characterization of Quantum Dots Conjugated with CA 125 Antibodies for Ovarian Cancer detection", filed Jun. 30, 2004.

GOVERNMENT SUPPORT

This invention was developed under support from the National Institute for Health and the National Cancer institute under grant PAR-01-019, and the National Science Foundation, DMI-0218967; accordingly the U.S. government has certain rights in the invention.

BACKGROUND OF THE INVENTION

Ovarian cancer is the most lethal gynecologic malignancy. This largely reflects the fact that approximately 75% of cases are detected at advanced stages of disease, when cure is unlikely. In contrast, 5-year survival for patients with early stage ovarian cancer can exceed 90%. It is possible therefore that detecting a greater number of patients with early stage disease by improving screening modalities could significantly improve overall survival.

To date, detection of the tumor marker CA 125 secreted from ovarian epithelium is the only biomarker available for screening. Detection of CA 125 antigen is based on ELISA and RIA assays used in serologic screening for ovarian cancer and monitoring patient therapeutic responses. However, the sensitivity of the current methods is approximately 70%, thereby greatly limiting its value in mass screening for the disease.

Lung cancer continues to be the most lethal malignancy, accounting for an estimated 160,000 deaths per year in the United States. This high mortality reflects the fact that the majority of cases are detected at advanced stages, when cure is unlikely. At the same time lung cancer is one of the most 'avoidable' causes of death worldwide. It is also one in which differences in relation to sex and gender especially significant. Increasing lung cancer deaths amongst women alongside stable or decreasing deaths amongst men in many countries have substantially altered the male:female ratio in this disease and produced a need to understand differences between men and women in lung cancer risk, and how they relate to sex and gender. The risk of lung cancer may be different for men and women in response to a complex interaction between biological factors such as hormonal difference and gendered factors such as smoking behavior. Women's apparently greater relative risk of lung cancer and the differences between men and women in the risk of specific histological types of lung cancer need to be understood from a perspective in which both biological influences and gender influences are drawn out.

Shifting detection to an early stage could significantly improve overall survival. Molecular methods, including application of sensitive and specific lung cancer biomarkers, are a promising strategy to achieve this goal. We propose a novel approach to increase the accuracy of early lung cancer detection through the application of nanotechnology, where lung cancer biomarkers, biochemically conjugated to fluorescent semiconductor nanocrystals called "quantum dots" (QD) are detected by a unique QD-immunometric methodology utilizing photoluminescence spectroscopy (PL).

Quantum Dots (QD) have attracted a great attention from the medicine/biology because of the advantages they offer over conventional organic dyes. Nanometer-sized semiconductor particles have been covalently linked to biorecognition molecules, i.e., antibodies, peptides, nucleic acids, or molecular ligands for application as fluorescent probes. Compared to organic dyes, quantum dots have unique optical and electronic properties, such as size- and composition-tunable fluorescence emission from visible to infrared wavelengths, large absorption coefficients across a wide spectral range and high levels of brightness and photostability. High-quality QDs were described recently in efficient optical multiplexing for in vivo cancer imaging using animal models. It was shown that biological tissues can be filters, which decrease QDs' absorbance at bluer wavelengths. Multicolor optical coding for oligonucleotides assay has been achieved by embedding different-sized QDs into polymeric microbeads. The use of ten intensity levels and six colors is supposed theoretically to code a million nucleic acid or protein sequences that can be developed for medical diagnostics. Bioconjugation of Quantum Dotes (QDs) involves the attachment of specific ligands, and represents the convolution of biotechnology and nanotechnology yielding hybrid materials, processes and devices.

Therefore, what is needed is a novel approach to increase the sensitivity and specificity of early detection of cancer through the application of nanotechnology, where luminescent semiconductor quantum dots (QDs) are conjugated with biomolecules.

SUMMARY OF INVENTION

In a general embodiment, the present invention includes a luminescent, bio-conjugate for use in the detection of cancerous and precancerous cells in a sample, or circulating cancer biomarkers detectable in body fluids (blood plasma, serum, sputum), comprising a luminescent semi-conductor nanoparticle and at least one biomarker associated with at least one cancer to be detected.

QDs are used as secondary antibody fragment conjugates, or joined via direct bioconjugation reaction with anti-biomarker primary antibody. The semi-conductor nanoparticle is preferably an inorganic semiconductor chosen from group consisting of Group II, Group III, Group IV, Group V, and Group VI. The biomarker is a protein (peptide) molecule recognized by antibody, such as a capture antibody, a detector antibody, or a combination thereof, associated with a cancer chosen from the group consisting of ovarian cancer, and non-small cell lung carcinomas. Generally, the biomarker is an antigen associated with at least one molecule chosen from the group consisting of CA125, ADAM10, H2BFQ, AASDHPPT, AB026190, DDX10, OPA1, EKI1, ZWINT, hTERT, VEGF, sIL-2, pSAT3, MAGE, MIF, and Osteopontin.

In an alternate embodiment, the present invention includes a luminescent, bio-conjugate for use in the detection of ovarian cancer, comprising a luminescent semi-conductor nanoparticle and at least one biomarker associated with ovarian cancer. The nanoparticles further comprise a core; and a shell forms a colloidal particle. In an illustrative embodiment, the core of the nanoparticle comprises CdSe and the shell comprises ZnS. Preferably, the QDs-probe for biomarker detection is an antibody associated with CA125.

In yet another embodiment, the present invention includes a luminescent, bio-conjugate for use in the detection of lung cancer, comprising a luminescent semi-conductor nanoparticle and at least one biomarker associated with lung cancer. The biomarker is an antigen associated with at least one molecule chosen from the group consisting of ADAM10, H2BFQ, AASDHPPT, AB026190, DDX10, OPA1, EKI1, ZWINT, hTERT, VEGF, sIL-2, pSAT3, MAGE, MIF, and Osteopontin.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Quantum Dot Conjugation

Figure 1:
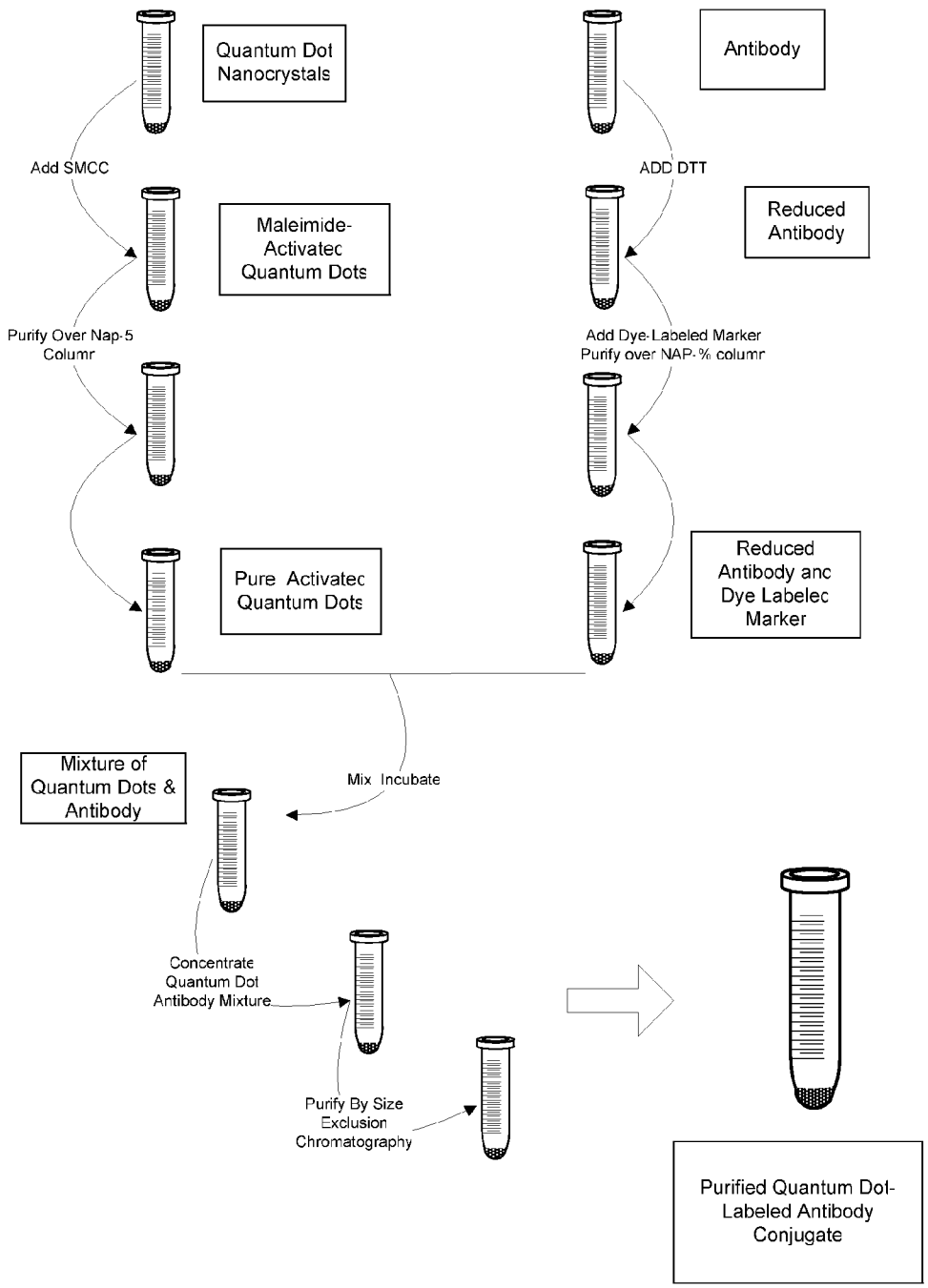
FIG. 1. Overview of the individual steps in the process of conjugating quantum dots to antibodies.

Conjugation kits are designed to allow the conjugation of antibodies to nanocrystals. The kit contains all necessary reagents and components for two conjugation reactions, as well as a detailed protocol. The conjugation uses a well-known chemistry based on the fast and efficient coupling of thiols to maleimide groups. Schematically, the overall process is shown in FIG. 1.

The first step in the conjugation process is the conversion of amines to thiol-reactive maleimide groups. This is achieved easily with the hetero-bifunctional crosslinker 4-(maleimidomethyl)-1-cyclohexanecarboxylic acid N-hydroxysuccinimide ester (SMCC). Following a 60 min reaction, the excess crosslinker is removed from the activated quantum dots by gel filtration chromatography.

The other component of the conjugation reaction is the antibody supplied by the user. This can be a whole IgG molecule or a F(ab')2 derivative. To generate thiol groups, the antibody is treated with dithiothreitol (DTT), which reduces some of the disulfide bonds of the starting antibody. Removal of the excess reducing reagent is also accomplished by gel filtration chromatography. To facilitate the identification of the antibody-containing fraction without the need for absorbance measurements, the kit provides a convenient dye-labeled marker molecule, which co-elutes with the reduced antibody. The fractions containing the dye are pooled and used in the next step. This dye-labeled marker does not interfere with the conjugation process and is easily removed from the final conjugate in the last purification step.

The maleimide-activated quantum dots are subsequently mixed with the thiol-containing antibody. The recommended molar ratio of antibodies to dots is approximately 3.2-4:1. The conjugation reaction is allowed to proceed for one hour and is followed by quenching of the excess maleimide groups with a dilution of β-mercaptoethanol.

The final step of the process is the removal of any remaining free, unconjugated antibody molecules from the quantum dot conjugate. This is achieved by size-exclusion chromatography over a small column filled with Superdex® 200. The Qdot Antibody Conjugation Kits include this material, as well as an empty, disposable plastic column for the actual separation. The user is required to fill this column with the Superdex 200 material and pre-equilibrate it with PBS buffer (not supplied). The conjugation reaction is concentrated by ultrafiltration to a small volume and loaded onto the prepared column. The conjugate is eluted with PBS and collected as a solution in about 100-120 µl of eluent. In this step, the dye-labeled marker is removed from the quantum dot conjugate and serves as a visual marker for the separation process. This material is essentially pure of free, unconjugated antibody and can be used directly, after a suitable dilution, in subsequent experiments.

The quantum dot-antibody conjugates generated with these kits can be used in all applications where the use of such conjugates has already been demonstrated, such as immunohistochemistry, tissue staining, ELISA, western blotting, flow cytometry and other, user-designed experiments. In addition to conjugation of antibodies, other thiol-containing molecules can be coupled to quantum dots using this kit. These include other proteins, thiolated oligonucleotides and peptides, and small molecules.

As mentioned, the luminescence stability and quantum efficiency of the bio-conjugated quantum dots are two major concerns presenting both fundamental interest and practical importance. The inventors show based on the performed study that the process of the QD's luminescence photo-quenching, which deteriorate the PL efficiency, can be substituted with the opposite effect of the PL enhancement in a proper experimental conditions. It is obvious that the PL enhancement is strongly beneficial specifically for the early cancer detection where low PL output is one of limiting factors of the luminescence biomarker methodology.

The effect of the QD luminescent photo-quenching was observed both in the photo- and cathodoluminescent experiments. The model explaining qualitatively the photo-bleaching PL kinetics was attributed to multi-photon generation of the electron-hole pairs (excitons) within the same QD and subsequent Auger recombination. The energy released after non-radiative Auger recombination of one exciton is transferred to the second exciton, which inject the electron into a long-life trap states in the ZnS matrix. This process leads to a local charging of the QD after the light exposure and reduction of the luminescence efficiency as proposed by Efros and co-workers.

An opposite effect is observed here, when the PL output in increased after light exposure. Considering possible mechanisms; First, the inventors emphasize that enhancement occurs both under UV (325 nm) and visible (488 nm) laser exposure. The latter has much smaller energy (2.54 eV) than ZnS band-gap and polymer is also transparent at this wavelength. Therefore, the effect follows a direct light absorption and electron-hole pair generation in the CdSe core. These pairs either recombine radiatively yielding the characteristic PL band, or alternatively can be captured by interface states which leads to their trapping or non-radiative recombination.

Figure 2:
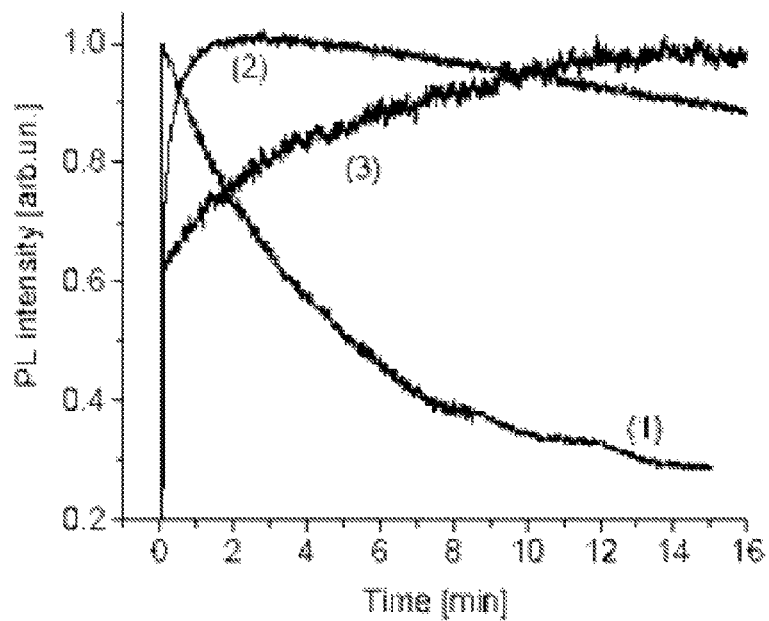
FIG. 2: PL intensity variation of the 655 nm luminescence band at room temperature and different laser power densities [W/cm]: (1)-500; (2)-20, (3)-0.2.

In summary, some specific features of the process. (1) It is observed only at high temperatures above 250K (FIG. 3): (2) the enhancement rate is increased when laser intensity goes up (FIG. 2); (3) it is observed in pure and bio-conjugated QDs; (4) rate, intensity and recovery depends on the origin of the conjugated bio-molecule and conjugation scheme. Keeping in mind (3) and (4) suggest that in the photo-enhancement process participate surface states (traps) at the CdSe/ZnS or ZnS/polymer interface.

Capture of the photo-carriers by these states may lead to (a) compensation of the electric charge and altering the electrostatic field around the QD, or (b) passivation of non-radiative centers due to chemical bond reconstruction, which represents a photo-chemical reaction. Carrier capture rate by the surface states is increased with increasing of the electron-hole photo-generation rate (excitation light intensity). This is observed in the experiment. A recovery of the initial state (with reduced PL intensity) is obviously accounted for thermal release of the carriers from the surface trapping states and depends on the ionization energy of the traps. This trap energy is strongly affected and altered by a coupling of the QD with bio-molecules and may lead to reversible and non-reversible PL enhancement effect.

QD's surface charge can reduce the exciton PL intensity. This can be a result of the exciton ionization in the external electric field as observed in photo-conductivity study of close-packed glassy solids of colloidal CdSe QDs. In the opposite case. compensation (neutralization) of the surface charge would lead to the PL increase due to stabilizing the exciton, increasing its binding energy. and reducing the PL thermal quenching. The inventors emphasize that if only one type of photo-generated carriers is captured and the other left on the QD level, the Auger mechanism would reduce PL intensity as predicted. Therefore, the inventors postulate that both electron and hole must be captured by spatially separated and charged donor (D+) and acceptor (A−) surface defects, correspondingly. This leads to the neutralization of these defects according to the reactions $$D^{+}+e => D^{\circ} \text{ (and) } A^{-}+h => A^{\circ}$$

and reduction of the surface charge (i.e. electric field), which reduces the exciton PL intensity. Alternatively, non-radiative recombination defects are eliminated as a result bond restructuring at the QD surface due to a photo-chemical reaction. In this case, the recovery of the PL enhancement process is caused by a thermal reconstruction of chemical bonds. More experiments are required to identify a particular mechanism of the PL enhancement.

In conclusions, the inventors provide a new effect of the luminescent enhancement in pure and bio-conjugated CdSe/ZnS core/shell quantum dots. The effect shows utility to enhance noticeably the QD quantum efficiency and to benefit the early cancer detection methodology based on QD bio-markers.

In a case of early cancer detection this approach offers the potential to detect molecules in biological samples at levels below $10^{-7}$. In one embodiment, the inventors conjugated core-shell CdSe/ZnS luminescence QDs with monoclonal mouse anti-CA 125 antibody (AB) as a potential serologic assay. Among different monoclonal antibodies potentially available for CA125 detection, we have selected OC-I25 for QD bioconjugation because it recognizes the defined peptide epitope of the target and can be compared with accepted clinical assays.

Tunable wavelength emission of the luminescence QDs was achieved from a variety of the inorganic semiconductors, predominantly of II-VI compounds such as CdSe, CdTe, CdS, etc. To obtain a noticeable quantum efficiency of the QD luminescence the core-shell structures can be effectively designed in a form of colloidal particles. A successful example represents CdSe/ZnS core/shell coupling, where large band-gap material (ZnS) serve as a surface passivating layer and as a barrier assisting the electron-hole confinement in the CdSe core. A stability and efficiency of the QD luminescence is a critical aspect. Under intense laser or electron beam illumination it was observed a dramatic degradation of the luminescence intensity attributed to ionization of nanocrystals and subsequent trapping of the ejected electrons in the surrounding semiconductor matrix. Therefore, even in the capped QDs with wide-gap semiconductor or embedded into ZnS matrix photo-degradation occurs. On the other hand, it was observed previously that the PL intensity is enhanced under light illumination in the bulk CdS and CdSe crystals. This was identified as light-induced defect reactions caused by donor-acceptor pair dissociation. assigned to a photo-chemical reaction. Similar effect of photo-induced PL enhancement was noticed in the glassy closed-packed film of QDs covered with ZnS film.

Immunocytochemistry, microscopy and imaging techniques are well-established methodologies used for protein marker assessment in clinical and experimental setting. For example, the inventors found that microscope-based image-analysis improved the sensitivity of standard sputum cytology 8-fold, yielding a specificity of 56% assessing lung cancer biomarker hnRNP A2/B1 in rare cells (1 out of 5000 normal sputum cells) (see Example II below). In other studies the inventors applied flow cytometry (FC) and laser scanning cytometry (LSC) for marker evaluation.

LSC uses lasers to excite fluorochrome labels in cellular specimens, detects the fluorescence in discrete wavelengths with multiple photomultiplier tubes, and offers software analysis tools similar to FC to obtain statistical data on populations of detected events. Slide-based LSC provides the opportunity to analyze substantially fewer cells while confirming cellular morphology by relocating individual cells. The process can be repeated to collect multi-spectral (multiple fluorophore) data, but the LSC instrument is slow, requiring 10 to 20 minutes to scan one slide containing a single sample.

EXAMPLE I

Ovarian Cancer

The inventors generated an assay prototype using the most widely accepted circulating biomarker for ovarian cancer—CA125. Development of the nano-assay was based on immunometric methodology with the use of available QDs that were used as secondary antibody QD-F(ab) fragment conjugate, or were subjected to direct bioconjugation reaction with anti-CA125 primary antibody. For direct conjugation of QDs with OC125 mouse monoclonal antibody (DAKO, Carpinteria, Calif.), the inventors used Qdot 655 Antibody Conjugation kit from Quantum Dot Corp. (Hayward, Calif.). The overall schema is: Si-wafer surface-anti-CA125 Ab (capture, clone M11)+Ag(CA 125)+anti-CA125 Ab (detector, clone OCI25-QD 655)-Read PL signal. PL spectrum from the Ag-Ab complex was measured utilizing described schema of solid phase sandwich format fluorometric assay and high-resolution PL spectroscopy, with confirmation of detected relative level of CA 125 in sample by reference ELISA.

The inventors utilized a capture (M11) and detector (OC125) antibody (Ab), designated as anti-epithelial ovarian carcinomas and as a reference standard the serial dilution of human CA 125 antigen (Ag) of high purity grade. Control wells/spots either lacked antigen or contained QDs 655-OC125 Abs only. The plasma samples from cancer patients were assayed using the reference ELISA kit for measurement of CA 125. The reportable (dynamic) range of CA 125 detectable by the nano-assay is 0 to 500 U/ml, which reflects the physiological range of CA 125 in blood. The samples for PL measurements represented—3 mm spots deposited on a clean Si-wafer surface as a substrate to minimize the luminescence background signal in the visible spectral range.

The PL spectroscopy was performed between 80K and room temperature, using a 50 mW HeCd laser line at 325 nm or 200 mW Ar+ laser line at 488 nm as the excitation sources. Laser power density varied by use of a set of calibrated neutral density filters and could be focused down to 100 microns spat. At low intensity measurements the laser beam was un-focused with approximately 1.5 mm laser spot diameter at the sample surface. The PL signal was collected by optics, dispersed by a SPEX SOOM spectrometer and recorded by a photo multiplier tube coupled with a lock-in amplifier. All system is computer controlled.

FIG. 2 presents luminescence kinetics of the bio-conjugated QDs measured at the maximum of the PL spectrum at 655 nm. The kinetic data are collected at various power densities of the 325 nm HeCd laser line which was used as the PL excitation source. At the highest laser power density of 500 W/cm2 (focused laser spat down to 100 microns), the inventors observed a strong photoquenching when the luminescence intensity degrades by a factor of three from its maximum value within 15 minutes (curve 1). At lower excitation power it is recognized that this photo-quenching follows an initial PL increase (hereafter, "photo-enhancement") as shown on curve (2). When the laser power density is reduced more, both the enhancement and quenching kinetics are slowing down. At substantially reduced laser power of a few W/cm$^2$ it is possible to clearly separate the enhancement part of the kinetics as illustrated by the curve (3) in FIG. 2. The inventors concentrated on the enhancement part of the PL kinetic curve, which is strongly motivated as a means to improve quantum efficiency of the bioconjugated QDs.

The following observations were depicted based on this time-dependent PL study. (1) PL photo-enhancement can be quite substantial spanning the range from 10% up to 4-fold with respect to the initial luminescence intensity. (2) PL enhancement is observed on both pure QDs and bio-conjugated QDs. The inventors noticed that bioconjugation affects noticeably a percentage of the enhancement and expand the process in time scale. In the bio-conjugated QDs the PL enhancement is typically stronger. (3) If the sample subjected to UV exposure was held in dark for definite time, the enhancement effect can be either fully recovered back (reversible effect) and the enhancement kinetics can be repeated again, or the effect can be non-reversible and show no recovery in the dark for at least 1 hour. Reversible behavior was found on QDs attached to F(ab) fragment used as a linkage molecule, while the non-reversible was observed on QDs without F(ab) bridge. (4) The enhancement effect is observed with both laser excitations at 325 nm (HeCd) and 488 nm (Ar+).

Figure 3:
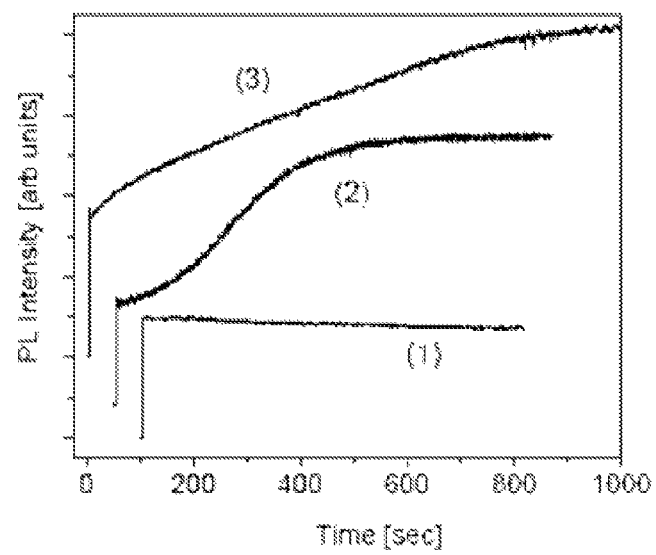
FIG. 3: Kinetics of the PL enhancement measured at different temperatures: (1)-150K; (2)-250K, (3)-300K.

FIG. 3 shows PL enhancement kinetic curves measured at different temperatures in the range from 80K to 300K. It is clear that PL enhancement effect is terminated at low temperatures and clearly observed at high temperatures. Specifically it is not found at temperatures in the range from 80K up to 210K and starts to be prominent in the range of 250K to 300K. It is interesting that the kinetic is not a single-exponential curve.

Figure 4:
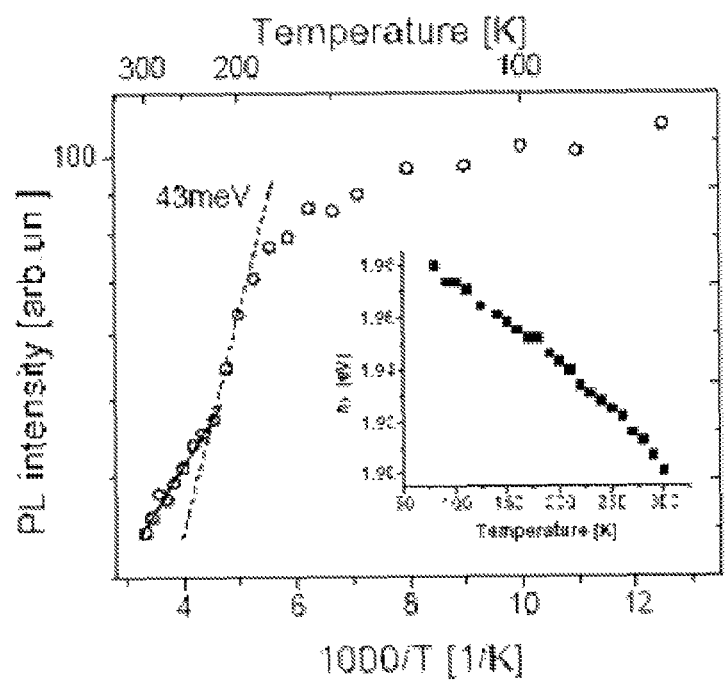
FIG. 4: Temperature dependence of the QD PL intensity in the bio-conjugated QDs with partial PL enhancement at temperatures above 218K.

The graph shown in FIG. 4 represents temperature dependence of the PL intensity of bio-conjugated QDs. The sample was cooled down to 80K in dark, and was exposed to 325 nm laser during heating cycle. The graph is plotted in the Arrhenius coordinates of the logarithmic PL intensity versus inverse temperature.

The following analytical dependence is typically describes the T-quenching of the PL intensity:

$$I(T) = I_0 \exp(E_a/k_b T)$$

where Ea is the characteristic activation energy of the T quenching process, k is the Boltzmann constant. Here, PL intensity shows exponential decline above 200K with $E_a$=43 meV (dotted line). The inventors observed also that the curve shows substantial variation of the exponential quenching part. which can he attributed to the photo-enhancement process described above. This matches to the results in FIG. 3. The temperature range of the PL enhancement according to the T-quenching curve is above 218K. In the insert the temperature dependence of the PL band maximum position is shown, which follows CdSe band edge temperature shift.

EXAMPLE II

Lung Cancer

Lung Cancer and Related Sex Differences

In earlier studies of lung cancer, it appeared that about 90 percent of the sex difference in mortality was attributable to smoking. The estimated contributions of smoking included both the effects of sex differences in smoking habits and the effects of sex differences in the increase in mortality caused by smoking, especially in men. Later epidemiological and biochemical studies have indicated that females may be at greater risk of smoking associated lung cancer compared with males. The lung cancer death rate for females increased by 266% from 1968 to 1999, whereas for males, it increased by 15%. Lung cancer now exceeds breast cancer as the leading cause of cancer death in women, and both incidence and mortality rates continue to climb. Most studies have reported that women receive diagnoses at a younger median age, suggesting that they have an increased susceptibility to the development of lung cancer. Henschke et al provided evidence that, for a given level of smoking, more women than men develop lung cancer, using baseline CT screening for lung cancer. However, not all studies support this observation and the effect of gender on the lung cancer risk associated with tobacco use remains unclear. Women who smoke appear to be at higher risk of developing small cell lung cancer than squamous cell lung cancer, whereas men who smoke have a similar risk for the two histologic conditions. Furthermore, women smokers are more likely to develop adenocarcinoma of the lung at younger age with better prognosis than males, and estrogens may play a causative role in this phenomenon. To characterize gender differences in lung cancer a retrospective study was conducted with analysis of all patients undergoing surgery for NSCLC in a single institution over a 20-year period. It was shown that compared with men (n=839), women (n=198) were more likely to be asymptomatic (32% vs 20%, P=0.006), nonsmokers (27% vs 2%, P<0.001), or light smokers (31 pack-years vs 52 pack-years; P<0.001). Squamous cell carcinoma predominated in men (65%), and adenocarcinoma predominated in women (54%). Preoperative bronchoscopy contributed more frequently to a histologic diagnosis in men (69% vs 49% in women, P<0.001), and fewer pneumonectomies were performed in women (22% vs 32% in men, P=0.01).

After multivariate Cox regression analysis. it was shown that women survived longer than men (hazard ratio, 0.72; 95% confidence interval, 0.56-0.92; P=0.009) independently of age, presence of symptoms, smoking habits, type of operation, histologic characteristics, and stage of disease. The protective effect linked to female sex was present in early-stage carcinoma (stage I and II and absent in more advanced-stage carcinoma (stage III and IV). These studies emphasize strong sex differences in presentation, management, and prognosis of patients with NSCLC. In a case-control study, data were examined for sex-race differences in the lung cancer risk associated with cigarette smoking. Results indicate that Kreyberg I Lung cancers (squamous cell and oat cell carcinomas) are associated with heavier intensity of smoking than Kreyberg II lung cancer (adenocarcinomas and alveolar cell carcinomas); blacks are at higher risk than whites (relative risk=1.8), and women are at higher risk than men for a given level of smoking (RR=1.7). These findings indicate the existence of important differences in the smoking-associated risk for lung cancer which depend upon sex, race, and histology.

Some of these differences can be explained by social behaviors, such as type of cigarettes, way of smoking, addiction to smoking. There are evidences of genetic predisposition to lung cancer, especially for women under age 50 at time of diagnosis. Genetic variation between men and women has been studied in genes encoding carcinogen metabolizing enzymes (CYP1A1) and glutathione-S-transferase genes, DNA repair proteins in nucleotide excision repair genes (oncogenes (K-ras, c-erbB-2), tumor suppressor gene p53 and growth factor receptors. Among lung cancer patients, female smokers have been found to have higher levels of PAH-related DNA adducts and CYP1A1 gene expression in their normal lung tissue compared to male smokers. A possible role of steroid hormones in these sex differences via interactions between aryl hydrocarbon receptor and estrogen receptor mediated cellular effects has been suggested, however obtained data do not support the hypothesis of a role of estrogen or the ER$\alpha$ in regulating the metabolic activation of polycyclic aromatic hydrocarbons in lung. CYP1A1 is involved in the metabolism of benzopyrene, a suspected lung carcinogen; it is therefore conceivable that genetically determined variations in its activity modify individual susceptibility to lung cancer.

The inventors also investigated the role of gender in pulmonary carcinogenesis by analysis of p53 mutations, immunohistochemistry, serum antibodies and c-erbB-2 expression in a series of 63 male and 44 female lung cancer patients whose tumors were resected at the Mayo Clinic between 1991 and 1992. Adenocarcinoma was the more frequent histological type in women (62%) than in men (41%). Sequence analysis of exons 5-8 in 42 females and 49 males identified 44 p53 mutations in 42 tumors (46%). Base substitution mutations showed a preponderance of G:C-->T:A transversions, which were more frequent in women than men (40 versus 25%) and in individuals exposed to asbestos. c-erbB-2 immunohistochemical staining was identified more frequently in females (nine cases) than males (two cases). Marked immunohistochemical staining for p53 positively correlated with the presence of mis-sense mutations in exons 5-8 (81%, P<0.001). Seven mis-sense mutations (four in exon 5, two in exon 6, one in exon 8) were identified in five of nine patients who had serum antibodies recognizing p53; tumors from these patients were also strongly positive for p53 by immunohistochemistry. These and other results indicate gender differences in the genetic and biochemical alterations in lung cancer and generate hypotheses regarding gender differences in lung cancer susceptibility.

Survival from lung cancer is related to stage at presentation. As localized tumors generally do not cause symptoms, the disease is usually diagnosed in symptomatic patients at advanced stages when the prognosis is poor. As a result, the overall 5-year lung cancer survival rate is only 14%; 48% for localized lung cancer and 4% for advanced stages. A most remarkable observation was made in that the favorable prognostic effect of the female gender was restricted to patients aged less than 60 years (ms 13.3 mo vs. 10.1 mo; 2 ys 26% vs. 5%), whereas for older women no advantages over men's results were established (ma 9.3 ml vs. 9.1 mo; 2 ys 6% vs. 7%).

A proportion of 32% of female patients with limited disease aged less than 60 years achieved a 3-year survival rate. It was concluded (a) that sex constitutes a major prognostic factor in SCLC and is especially useful as a predictor for long-term survival, and (b) that the favorable prognostic value of the female sex is restricted to younger patients.

Lung Cancer and Sex Related Informative Biomolecules.

The most convincing unifying theory for explanation of sex differences in lung cancer presentation and susceptibility at the genetic and biochemical levels is that estrogen is involved in these effects. Women have a naturally higher circulating estrogen level than men, and this difference may contribute to their increased susceptibility to lung cancer. In support of this theory there are evidences that early age of menopause decreases risk of adenocarcinoma of the lung, whereas hormone replacement therapy is associated with higher risk of lung cancer, also increasing by smoking. Recent studies provide evidence that estrogen-signaling pathways play an important role in normal lung biology and in controlling the growth of lung cancer estradiol has been reported to stimulate proliferation of some but not all cell lines, whereas the antiestrogen ICI 182,780 consistently inhibits growth in vitro and in vivo.

Transgenic mice harboring an estrogen-regulated luciferase reporter construct display a 5-fold increase in luciferase activity in the lung upon estradiol treatment, indicating that the lung is a hormone-responsive tissue. There is an opinion that estrogen may promote lung cancer through direct actions on pre-cancer or cancer cells, or through indirect action on lung fibroblasts. Estrogen levels are often elevated in female lung patients compared with women without lung cancer. Estrogens may also be produced locally in men through cytochrome P-450 enzyme complex aromatase. Blocking the effects of estrogen might be an important therapeutic strategy against lung cancer in both sexes, especially targeting estrogen receptors mediating cellular response to estrogen. Two estrogen receptors. ER$\alpha$ and ER have been identified, which are encoded by separate genes, and function as ilgand-activated transcription factors.

ER$\beta$ is the dominant form in lung: transcripts are detected in the majority of NSCLC cases examined, protein is detected by immunoblot and immunohistochemistry reveals a predominantly nuclear localization, which is consistent with its role as a nuclear transcription factor. Furthermore, targeted inactivation of ER$\beta$ results in lung abnormalities in female mice, including a decrease in the number of alveoli and altered surfactant homeostasis. ER$\beta$ Immunostaining was found more often in adenocarcinomas, compared to squamous cell carcinomas. The predominance of ER$\beta$ in the lung and the fact that estrogens can stimulate lung tumor growth are intriguing and opposite from ER$\beta$ inhibitory effect in the carcinogenesis of other tissues, as mammary and prostate. The mechanisms of these observations are unknown, it is thought to occur through the function of ER$\alpha$.

Estrogens may also affect lung cancer growth clinically as full estrogen blockade, achieved through inhibition of estrogen biosynthesis with the aromatase inhibitor, exemestane, reduces the occurrence of primary lung cancer in women with breast cancer as compared with tamoxifen, an agent that displays ER partial agonist activity in certain tissue. Prior studies employing exogenous estrogen-regulated reporter constructs suggest that NSCLC cells possess the components necessary to generate ER-mediated transcription responses.

Recently it was shown using gene mini-arrays, that ER ligands have the capacity to regulate endogenous gene expression in NSCLC cells. Expression profiles were examined after treatment with ER agonist 17-β-estradiol, the pure ER antagonist (Faslodex), or EGF, which served as a positive control for an alternative growth stimulus. E-cadherin and inhibitor of differentiation 2 were differentially regulated by 17-β-estradiol versus Faslodex. EGF also stimulated proliferation of NSCLC cells but had no effect on expression of E-cadherin and inhibitor of differentiation 2, suggesting they are specific targets of ER signaling. Recent studies from this group suggest that estrogen can directly stimulate the transcription of estrogen-responsive genes in the nucleus of lung cells, and utilize rapid stimulation of phospho-p44/p42 MAPK signaling. Interestingly, data suggests that nicotine signals through neuronal nicotinic acetylcholine receptors may cause proliferation of human bronchial cells, and involve activation of phospho-p44/p42 MAPK family of kinases.

Novel Potential Lung Cancer Biomarkers

Phosphorylated Histone H2AX-γ-H2AX: Histone H2AX is a minor variant of the highly conserved histone H2A that is part of the histone octamer in the core of the nucleosome in eukaryotic genomes, H2AX differs from H2A and all the other human H2A variants by having a longer carboxy-terminal tail that contains an SQE motif, a consensus site for phosphorylation by P13K-related kinases such as ATM, ATR and DNA-PK. Following induction of double strand breaks (DSB) by ionizing radiation ATM phosphorylates H2AX at Serine 139 (part of the SQE motif). This residue is also phosphorylated by ATR in response to ultraviolet light or replication stress. γ-H2AX localizes specifically at sites of damage and it has been recognized as one of the earliest markers of DNA damage. Immunofluorescence studies have shown that several proteins involved in DNA repair including BRCAI, BRCA2, Rad5I and Mre11 are recruited to sites of γ-H2AX. Recent data suggests that H2AX is a tumor suppressor gene, raising the possibility that mutations or changes in levels of H2AX may be causally involved in cancer development. Monteiro, at al demonstrated absence of constitutional H2AX gene mutations in 101 breast cancer families, supporting opinion that in the population as a whole mutations in the H2AX are not associated with breast cancer risk. It is therefore clear that H2AX plays a central role in the cellular response to DNA damage and may underlie (epi) genetic predisposition to cancer.

The use of γ-H2AX as a biomarker in lung cancer and developing of nano-probes for its detection, have at least three important advantages: First, it constitutes a common event resulting from a variety of endogenous and exogenous DNA damage stimuli. Endogenous stimuli such as stalled replication forks, presence of reactive oxygen species leading to DNA damage or frequent breaks in genomic unstable cells are all hallmarks of cancer cells and will trigger phosphorylation of H2AX. This provides a basis for the broad use of γ-H2AX as a biomarker for cancer. Likewise, exogenous stimuli, such as treatments with radiotherapy and chemotherapy drugs will also trigger phosphorylation of H2AX. Second, it has been shown that phosphorylation of H2AX is linearly correlated to the number of breaks. That opens the possibility that with an automated quantitative method one can discriminate between different phases in the evolution of the malignant phenotype, from normal, preneoplastic, to neoplastic and highly aggressive tumors. Third, it is the most sensitive marker of DNA damage known, being able to detect very low radiation doses (~1 mGy) and current data suggests that some low level of damage (exogenous or endogenous) may go unrepaired for several days.

The inventors propose the use of fluorescent semiconductor nanocrystals (QD) to increase sensitivity, whereas the use of traditional biomarkers display some weakness due to a lack of detection sensitivity or specificity. Here, because γ-H2AX can detect very low damage it is possible to greatly improve detection to include very low levels of damage that are intrinsically different from normal cells but still below the sensitivity threshold of traditional antibody-based detection techniques. This will allow for the detection of cancer cells at very early stages—a goal that has constantly eluded researchers.

In summary, these three important strengths and the preliminary data show that γ-H2AX constitutes a promising biomarker for lung cancer progression, and its expression and/or phosphorylation in lung cancer may be triggered by estrogen effect.

Type-specific cytokeratins: Progression of metaplasia and hyperplasia in bronchial and bronchiolo-alveolar epithelium to atypical premalignant lung lesions may induce acquisition of intermediate-size keratins typically expressed in simple epithelia and non-squamous cancers, i.e., peripheral adenocarcinomas. Intermediate-size cytokeratin 7 is expressed n normal bronchial and bronchiolar epithelium of the lung, and lung adenocarcirtomas. Intermediate-size cytokeratin 8 has been reported to be expressed in lung cancers, and its expression correlated with increased invasiveness of the tumor in vitro and in vivo. Increasing values of cytokeratin 8 in sera were significantly associated with tumor progression and decreased survival in patients with NSCLC. RT-PCR analysis of lung cancer cell lines indicate that lung cancer cells resistant to apoptosis express aberrant messenger RNA splicing of cytokeratin 8. The inventors found higher CDC6 expression (marker of DNA replication) in cytokeratin subtypes-specific exfoliated sputum epithelial cells from preclinical specimens collected from cases than controls within the Moffitt lung screening study. Thus, capturing cells expressing intermediate cytokeratins 7/8 may allow detection of rare proliferating cells, a potentially valuable application for early lung cancer detection.

The inventors used a multi-fluorescent labeling technique and the laser scanning cytometry (LSC) to identify epithelial cells of interest and quantify the expression of CDC6 protein within cytokeratin-type specific positively gated cells. The data provide evidence for the increased proportion of proliferating epithelial cells in pre-clinical sputum specimens from patients later diagnosed with bronchogenic carcinomas and demonstrate the ability of LSC to detect cells of interest in preserved sputum samples.

Biomarkers Identified Through Gene Expression Profiling of LCM Cells

The inventors performed gene expression profiling of laser-capture microdissected cells (malignant, pre-malignant (atypical), and normal) from 5 lung tumors (3 females and 2 males cases), and corresponding (adjacent to tumor) non-involved lung tissue. They used Affymetrix HG-133A chips and analyzed the data with Affymetrix suitwork 5.0 (Moffitt microarray core). These findings were confirmed through gene expression profiling of lung tumor/normal samples from 50 patients. They then applied a variety of bioinformatics approaches to develop a list of the top 12 over-expressed genes as additional potential lung-cancer specific biomarkers. The list was reduced by excluding ESTs or splice variants with unknown function. Although each of these markers may be useful in the early detection of lung cancer, two on the list are particularly promising based on their known function, and higher degree of expression was found in females cases.

RAB2 is a member of the rab branch of the ras superfamily of oncoproteins and ras-related proteins. It is frequently over-expressed in peripheral blood mononuclear cells from patients with solid neoplasms, and fluctuates during the course of therapy. Pre-mRNA splicing factor (SFRS1) belongs to the family of non-snRNP splicing factors, and is characterized by the presence of an RNA recognition motif and a serine- and arginine-rich (SR) domain. SR proteins are required at early stages of spliceosome assembly. Pre-mRNA processing is an important mechanism for globally modifying cellular protein composition during tumorigenesis. Expression of two key pre-mRNA alternative splicing factors was compared in a mouse model of early lung carcinogenesis and during regenerative growth following reversible lung injury. Heterogeneous nuclear ribonucleoprotein (hnRNP) AI and alternative splicing factor/splicing factor 2 (ASF/SF2)-SFRS1 act antagonistically to modulate splice site selection.

Both hnRNP AI and ASF/SF2 contents rose in adenomas and during injury-induced hyperplasia compared to control lungs, as measured by immunoblotting.

Immunohistochemical analysis showed that hnRNP AI localized exclusively within tumor nuclei, while SFRS1 appeared in cytoplasm and/or nuclei, depending on the growth pattern of the tumor cells. The complete list is given in Table 1 and 2.

TABLE 1

Top 12 Genes overexpressed in microdissected lung malignant/pre-malignant cells

| Gene Symbol | Gene Name | Unigene Number | Accession Number |
|---|---|---|---|
| SFRS1 | splicing factor, arginine/serine-rich 1 (splicing factor 2, alternate splicing factor) | Hs.73737 | NM_006924 |
| AASDHPPT | aminoadipate-semialdehyde dehydrogenase-phosphopantetheinyl transferase | Hs.64595 | NM_015423 |
| ADAM10 | a disintegrin and metalloproteinase domain 10 | Hs.172028 | NM_001110 |
| H2BFQ | H2B histone family, member Q | Hs.2178 | NM_003528 |
| ZWINT | ZW10 interactor | Hs.42650 | NM_007057 |
| AB026190 | Kelch motif containing protein | Hs.106290 | NM_014458 |
| BF343007 | transcription factor AP-2 alpha (activating enhancer binding protein 2 alpha) | Hs.334334 | BF343007 |
| DDX10 | DEAD/H (Asp-Glu-Ala-Asp/His) box polypeptide 10 (RNA helicase) | Hs.41706 | NM_004398 |
| RAB2 | RAB2, member RAS oncogene family | Hs.78305 | NM_002865 |
| OPA1 | optic atrophy 1 (autosomal dominant) | Hs.147946 | NM_015560 |
| AK024896 | FLJ21243 (detects an unusual termination site or splice variant of mitochondrial protein S6) | Hs.268016 | AK024896.1 |
| EKI1 | ethanolamine kinase | Hs.120439 | NM_018638 |

Protein Markers in Blood

Markers detectable in serum/plasma are attractive because of their accessibility. From the list of known lung cancer circulating biomarkers (Working Classification of Lung Tumor Markers (NSCLC+SCLC), the inventors selected five for the proposed project: hTERT; CAI25 (MUC 16); VEGF, sIL-2, and added Osteopontin. The following describes the potential of these markers for early lung cancer detection with more detail.

TABLE 2

Lung cancer biomarkers selected for the proposed project and relative antibodies

| Biomarker | Antibody Clone | Manufacturer | Type |
|---|---|---|---|
| hTERT | 44F12 | Novocastra, Newcastle upon Tyne. UK | Mouse, monoclonal |
| CA125 | 0C125 | DAKO Cytomaton, Carpinteria, CA | Mouse, monoclonal |
| VEGF | Ab array | Neomarkers Inc., Fremont, CA | Mouse, monoclonal |
| sIL-2R-alpha | Ab array | Hemicon Int., Temulca, CA | Mouse, monoclonal |
| CDC6 | 37F4 | Molecular Probes, Eugene, OR | Mouse, monoclonal |
| Cytokeratin 7 | OV-TL 12/30 | DAKO Cytomaton, Carpinteria, CA | Mouse, monoclonal |
| Cytokeratin 8 | 35βH11 | DAKO Cytomaton, Carpinteria, CA | Mouse, monoclonal |
| p-STAT3 | p-Stat3 (Tyr705) | Cell Signaling Technology, Beverly, MA | Rabbit, polyclonal |
| p-histone H2AX | p-H2AX (Ser139) | Upstate, Lake Placid, NY | Rabbit, polyclonal |
| Histone H2B(ac) | AHP421 | Serotec, Kidlington, Oxford, UK | Rabbit, polyclonal |
| ADAM10 | Anti-Human Adam 10 | Serotec, Kidlington, Oxford, UK | Rabbit, polyclonal |
| Rab2 | Anti-rab2 | Abcam Ltd. (ab794) | Rabbit, polyclonal |
| Osteopontin | Anti-human o-17 | Assay Designs, Michigan | Rabbit, polyclonal |

ADAM10 The 'a disintegrin and metalloprotease" (ADAM) family contributes to regulation of the cell-cell and cell-matrix interactions that are critical determinants of malignancy. ADAM-10 mRNA was detected in prostate cancer cell lines. ADAM-10 protein expression was found localized to the secretory cells of prostate glands with additional basal cell expression in benign glands. ADAM-10 protein was predominantly membrane bound in benign glands but showed marked nuclear localization in cancer glands. By Western blot, the 100-kDa profom and the 60-kDa active form of ADAM-10 were synergistically up-regulated in cells treated with insulin-like growth factor I plus 5alpha-dihydrotestosterone. Epidermal growth factor also up-regulates both ADAM-10 mRNA and protein. This study described for the first time the expression, regulation, and cellular localization of ADAM-10 protein in prostate cancer cell lines. The regulation and membrane localization of ADAM-10 supports the hypothesis that ADAM-10 has a role in extracellular matrix maintenance and cell invasion.

H2BFQ Histones H2A and H2B are known to be reversibly post-translationally modified by ubiquitination. It was observed in cultured ovarian carcinoma cells that proteasome inhibition stabilizes polyubiquitinated proteins, depletes unconjugated ubiquitin, and thereby promotes the deubiquitination of nucleosomal histones in chromatin. Provocative indirect evidence suggests that histone ubiquitination/deubiquitination cycles alter chromatin structure, which may limit accessibility of DNA repair proteins to damaged sites. In lung cancer Histone H2B was demonstrated to be an immunoreactive material recognized by the human monoclonal antibody HB4C5, which had been already established to be specific for lung cancers. The lung cancer-associated human monoclonal antibody HB4C5, which recognizes histone H2B as the antigen, accumulates specifically to the necrotic fraction of tumor. The uptake is enhanced by removal of N-terminal glycosyl residues from the antigen-binding site of the light chain. The inhibitory effect of histone H2B on the activity of HB4C5 antibody to immunostain the cytoplasmic antigen in lung adenocarcinoma tissue indicated that histone H2B at least had antigenic determinant comparable to the cytoplasmic antigen. A mouse anti-histone H2B monoclonal antibody could immunostain the cytoplasm of lung adenocarcinoma cells in sliced tissue sections in the same manner as the human monoclonal antibody HB4C5. An ELISA method for serodiagnosis of cancers was developed by employing histone H2B. This method measures anti-histone H2B antibody levels in patient sera. An assay of HB4C5 antibody on plastic immunoplates coated with histone H2B also showed specific reactivity of this antibody with histone H2B, and the reaction was effectively inhibited when extra histone H2B or mouse anti-histone H2B monoclonal antibody was added to the reaction mixture. These results consistently lead authors to a conclusion that histone H2B possesses antigenicity to the human monoclonal antibody HB4C5. By this method cancer patients were discriminated from normal healthy subjects at detection rates of 37% for lung cancer, 33% for liver cancer, 50% for pancreatic cancer, 42% for colon cancer, and 78% for cervical cancer. However, stomach and esophagus cancers showed detection rates of less than 17%, which are comparable to the values for benign diseases. It is likely that this assay method detects squamous cell carcinomas at relatively high rates.

AASDHPPT The protein encoded by this gene is similar to *Saccharomyces cerevisiae* LYS5, which is required for the activation of the alpha-aminoadipate dehydrogenase in the biosynthetic pathway of lysirie. Yeast alpha-aminoadipate dehydrogenase converts alpha-biosynthetic-aminoadipate semialdehyde to alphaminoadipate. It has been suggested that defects in the human gene result in pipecolic acidemia. In mammals, L-lysine is first catabolized to alpha-aminoadipate semialdehyde by the bifunctional enzyme alphaminoadipate semialdehyde synthase (ASS), followed by a conversion to alpha-aminoadipate by alphaminoadipate semialdehyde dehydrogenase. In Northern blot analysis the cDNA hybridizes to a single transcript of approximately 3 kb in all tissues except testis, where there is an additional transcript of 1.5 kb. Expression is highest in brain followed by heart and skeletal muscle, and to a lesser extent in liver. Function of this gene is known or inferred.

AB026190 Alternate Symbols: KLEIP, KLHLX, gene product is kelch-like 20. It has been shown that KLEIP interacted with F-actin and was concentrated at cell-cell contact sites of Madin-Darby canine kidney cells, where it colocatized with F-actin. Interestingly, this localization took place transiently during the induction of cell-cell contact and was not seen at mature junction.

DDX10 Product of this gene is DEAD (Asp-Glu-Ala-Asp) box polypeptide 10. DEAD box proteins, characterized by the conserved motif Asp-Glu-Ala-Asp (DEAD), are putative RNA helicases. They are implicated in a number of cellular processes involving alteration of RNA secondary structure such as translation initiation, nuclear and mitochondrial splicing, and ribosome and spliceosome assembly. Based on their distribution patterns, some members of this family are believed to be involved in embryogenesis, spermatogenesis, and cellular growth and division. This gone encodes a DEAD box protein, and it may be involved in ribosome assembly. Fusion of this gene and the nucleoporin gene, NUP98, by inversion 11 (p15q22) chromosome translocation is found in the patients with de novo or therapy-related myeloid malignancies.

OPAI This gene product: optic atrophy 1 isoform 1-8, is a nuclear-encoded mitochondrial protein with similarity to dynamin-related GTPases. It is a component of the mitochondrial network. Mutations in this gene have been associated with optic atrophy type I which is a dominantly inherited optic neuropathy resulting in progressive loss of visual acuity, leading in many cases to legal blindness. Eight transcript variants encoding different isoforms, resulting from alternative splicing of exon 4 and two novel exons named 4b and 5b, have been reported for this gene. Although OPAI is a nuclear gene, the gene product localizes to mitochondria, suggesting that mitochondrial dysfunction may be the final common pathway for many forms of syndromic and nonsyndromic optic atrophy, hearing loss, and external ophthalmoplegia. OPAI gene also acts as a marker for normal tension glaucoma (NTG).

EKI1 This gene encodes ethanolamine kinase, which is the first committed step in phosphatidylethanolamine synthesis via the CDP-ethanolamine pathway. This cytosolic enzyme is specific for ethanolamine and exhibits negligible kinase activity on choline. EKI1 maps to the telomeric region of the restricted I2p amplification in testicular germ cell tumors (TGCTs). Interestingly, ethanolamine kinase-overexpressing cells are protected against apoptotic cell death. It has been shown that DAD-R, SOX5, and EKI1 are expressed at relatively low levels in testicular parenchyma samples and that the expression levels of DAD-R and EKI1 are independent of the presence of spermatogenesis or carcinoma in situ (CIS). Although all three genes show higher expression levels in invasive testicular germ cell tumors (TGCTs), DAD-R shows a specific and significant increased expression in seminomas with the restricted 12p amplification and nonseminomas without this amplification.

ZWINT Alternate symbol: HZwint-1. Gene with protein product, function known or inferred.

Protein Markers in Blood hTERT Human telomerase reverse transcriptase is a ribonucleoprotein DNA polymerase that maintains the telomeric region of human chromosomes. Expression of hTERT has been observed in up to 100% of lung cancer tissues. Analysis of plasma DNA using RT-PCR of hTERT in 100 NSCLC patients revealed levels elevated 8-fold relative to smoking-matched controls. Brambilla et al analyzed recently expression of hTERT by immunohistochemistry in lung cancer tissue using commercially available antibodies and compared results with the standard PCR-based TRAP assay. Telomerase expression and pattern were distinctive among histopathological classes of lung cancer.

CA 125 (MUC 16) Mucins comprise a family of high molecular weight glycoproteins with a large number of O-glycosylated tandem repeat domains varying in number, length and extent of O-glycosylation. In lung cancer three tumor markers (CEA, CYFRA 21.1 and CA125) were evaluated for diagnostic sensitivity in newly diagnosed, untreated NSCLC. This study and others support their potential use as a circulating marker for NSCLC. Further measurements, including specificity studies in benign lung diseases, should be performed to confirm these results.

VEGF Angiogenesis is critical for the growth, progression, and metastasis of solid tumors. A high degree of tumor angiogenesis has been shown to correlate with poor survival in patients with lung cancer, especially those with early stage disease. VEGF is a 34- to 50-kDa dimeric, disulfide-linked glycoprotein synthesized by normal and neoplastic cells. Through binding to the specific membrane tyrosine kinase receptors that are expressed in vascular endothelial cells, VEGF has been shown to be an important regulator of tumor angiogenesis. Serum VEGF-C was found recently as a reliable marker for lymph node metastasis in NSCLC. Serum VEGF-C evaluation and CT examination were found to be complimentary to each other for accurate lymph node staging in NSCLC.

sIL-2 Interleukin-2 is a cytokine released by T lymphocytes that have become activated following presentation of antigens to the major histocompatibility complex (MHC). IL-2 then binds to the receptor IL-2R, a polypeptide consisting of three forms—alpha, beta and gamma. The alpha form of the IL-2R (55 kDa) only appears following T-cell activation, whereby it is cleaved off the surface of the T-cell, giving rise to a 45 kDa soluble product sIL-2Ra. Elevated levels of sIL-2Ra have been identified in sera from patients with lung cancer compared to healthy controls. The sIL2-Ra appears to be particularly useful for prognosis of lung cancer and patient survival.

Other Useful Markers pSTAT3 Signal transducers and activators of transcription (STAT) proteins belong to a family of cytoplasmic transcription factors controlling cellular proliferation, differentiation, development, inflammation and apoptosis in response to cytokines and growth factors. Despite a large body of evidence pointing to their potential importance, few direct studies into the role of STAT pathways in human lung cancer have been undertaken. Investigators from the Moffitt Cancer Center showed that multiple NSCLC cell lines demonstrate constitutive StatS DNA-binding activity, sensitive to pharmacological inhibitors.

MAGE MAGE genes belong to the family of cancer/testis antigens, and are known to be the most tumor-specific markers so far. Individual members of the melanoma antigen (MAGE) family are found frequently expressed in lung cancers of different histologic types. There are findings that MAGE expression has been changed in normal appearing lung tissue adjacent to lung cancer. There is an opinion that expression of MAGE genes seems to be an early event in lung carcinogenesis. The use of RT-PCR and TMA in analysis of MAGE expression in induced sputum and BAL specimens collected from former smokers demonstrated the potential to use it as a marker for detection pre-neoplastic lesions in the lung.

MIF Macrophage Migration Inhibitory Factor was selected as the target on the basis of reports that this antigen is often expressed in cancer, including lung cancer. MIF is one of the principal mitogenic mediators involved in cell proliferation, and its overexpression during neoplastic transformation may contribute to proinflammatory and tumor growth-associated angiogenic properties. In a previous SELDI-TOF MS study of malignant/premalignant lung, lung tumor-specific protein profiles with distinct peaks at the 12- to 23-kDa mass range were detected. Campa and Patz investigated lung cancer-specific protein profiles by MALDI-TOF-MS and found peaks in a similar mass range. One of the ion peaks at m/z 12338 was identified as MIF protein, a finding that was confirmed by Western blotting and immunohistochemistry.

Osteopontin Osteopontiri (OPN) is a phosphorylated, an integrin-binding, transformation-associated glycoprotein with diverse functions including cancer development, progression and metastasis. Its expression is induced by a variety of stimuli, including TNF-alpha and Ras proto-oncogene. Little is known about the significance of OPN expression in human cancers. Findings suggest that CD44 acts as a cell surface receptor for OPN and hyaluronate. It was shown that expression of isoform CD44S is altered in NSCLC, suggesting that CD44S down-regulation may confer a protective advantage of allowing escape from tumoricidal effector cells including activated macrophages and produced by them OPN. Differential OPN expression and its regulation in each histologic type of lung cancer are not well established. Available data suggest that OPN is especially expressed among squamous cell carcinoma of the lung with less frequency in other histologic types of NSCLC. Ras-p21 was shown co-expressed with OPN, which may suggest that OPN expression tightly regulated by Ras oncogene, and its concomitant induction with Ras activation may play a crucial role in the development of squamous cell carcinoma of the lung.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A luminescent, bio-conjugate for use in the detection of cancerous and precancerous biomarkers in a sample, comprising:

a luminescent semi-conductor nanoparticle;
wherein the nanoparticle is photo-enhanced with electromagnetic energy at between 325 nm and 488 nm, thereby generating electron-hole carrier pairs; and
at least one antibody associated with at least one cancer to be detected.

2. The bio-conjugate of claim 1 where the nanoparticle is a detector antibody fragment conjugate.

3. The bio-conjugate of claim 1 where the nanoparticles further comprise a core and a shell which form a colloidal particle.

4. The bio-conjugate of claim 1 where the biomarker further comprises an antigen recognized by the antibody which is selected from the group consisting of capture antibodies; and detector antibodies.

5. The bio-conjugate of claim 1 wherein the biomarker is an antigen associated with at least one molecule chosen from the group consisting of CA125, ADAM10, H2BFQ, AASDH-PPT, AB026190, DDX10, OPA1, EKI1, ZWINT, hTERT, VEGF, sIL-2, pSAT3, MAGE, MIF, and Osteopontin.

6. A luminescent, bio-conjugate for use in the detection of ovarian cancer, comprising:
a luminescent semi-conductor nanoparticle;
wherein the nanoparticle is photo-enhanced with electromagnetic energy at between 325 nm and 488 nm, thereby generating electron-hole carrier pairs; and
at least one antibody associated with a biomarker for ovarian cancer.

7. The bio-conjugate of claim 6 wherein the nanoparticle is a detector antibody fragment conjugate.

8. The bio-conjugate of claim 6 wherein the nanoparticles further comprise a core and a shell which form a colloidal particle.

9. The bio-conjugate of claim 6 wherein the antibody is chosen from the group consisting of capture antibodies and detector antibodies.

10. The bio-conjugate of claim 6 wherein the antibody is associated with CA125.

* * * * *